United States Patent
Sun

(10) Patent No.: US 12,186,461 B2
(45) Date of Patent: Jan. 7, 2025

(54) DISINFECTION PURIFIER

(71) Applicant: NINGBO MBV KANGMEI TECHNOLOGY CO., LTD, Zhejiang (CN)

(72) Inventor: Jianli Sun, Zhejiang (CN)

(73) Assignee: NINGBO MBV KANGMEI TECHNOLOGY CO., LTD, Yuyao (CN)

( * ) Notice: Subject to any disclaimer, the term of this patent is extended or adjusted under 35 U.S.C. 154(b) by 342 days.

(21) Appl. No.: 17/727,751

(22) Filed: Apr. 24, 2022

(65) Prior Publication Data

US 2022/0395606 A1  Dec. 15, 2022

(30) Foreign Application Priority Data

Jun. 10, 2021 (CN) .......................... 202110648911.5

(51) Int. Cl.
*A61L 9/20* (2006.01)
(52) U.S. Cl.
CPC ............. *A61L 9/20* (2013.01); *A61L 2209/11* (2013.01); *A61L 2209/14* (2013.01)
(58) Field of Classification Search
CPC ........ A61L 9/20; A61L 9/014; A61L 2209/11; A61L 2209/12; A61L 2209/14; A61L 2209/22; A61L 2209/111; B01D 46/2403; Y02A 50/20

See application file for complete search history.

(56) References Cited

U.S. PATENT DOCUMENTS

| | | | |
|---|---|---|---|
| 11,813,379 B2* | 11/2023 | Ke | ............................ A61L 9/20 |
| 2018/0021468 A1* | 1/2018 | Kim | ...................... F24F 1/0047 |
| | | | 250/436 |
| 2022/0016558 A1* | 1/2022 | Hendriksen | .......... B01D 46/521 |

FOREIGN PATENT DOCUMENTS

| | | |
|---|---|---|
| CN | 204115109 A | 1/2015 |
| CN | 204437864 U | 7/2015 |
| CN | 206065962 U | 4/2017 |
| CN | 211716745 U | 10/2020 |
| CN | 215962665 U | 3/2022 |
| GB | 1421267 A | 1/1976 |
| TW | M329402 U | 4/2008 |

* cited by examiner

*Primary Examiner* — David E Smith
*Assistant Examiner* — Hsien C Tsai
(74) *Attorney, Agent, or Firm* — Samson G. Yu

(57) ABSTRACT

Some embodiments of the present disclosure disclose a novel disinfection purifier. The novel disinfection purifier includes: a purifier housing, and a purification device body and an air suction device disposed inside the purifier housing. Air passes through the purification device body by means of the air suction device and is sterilized. An air inlet is provided on a side wall of the purifier housing, or an air inlet is provided on a bottom of the purifier housing, or an air inlet is provided on a side wall of the purifier housing and a bottom of the purifier housing, and an air outlet is provided on a top of the purifier housing. The purification device body includes a disinfection portion and a filter portion sleeving an outside of the disinfection portion.

15 Claims, 21 Drawing Sheets

DISINFECTION PURIFIER

CROSS-REFERENCE TO RELATED APPLICATIONS

The present disclosure claims priority to Chinese Patent Application No. 202110648911.5, filed on Jun. 10, 2021 and entitled "Novel Disinfection Purifier", the contents of which are hereby incorporated by reference in its entirety.

TECHNICAL FIELD

The present disclosure relates to a technical field of purification disinfection devices, and more particularly to a novel disinfection purifier.

BACKGROUND

With a deepening of an industrialization process, more and more severe environmental challenges arise. In recent years, continuous hazy weather has troubled many people, and has also aroused more and more attention. People pay more and more attention to health problems caused by air pollution. A quality of indoor air is crucial. Therefore, air purifiers have been popular with more and more people, and have gradually moved to a line of life necessities, which can absorb, decompose or convert various air pollutants, and can effectively improve air cleanliness. Air purifiers known to inventors generally treat pollutants in the air by means of filtration, adsorption, and the like, while bacteria in the air or bacteria growing inside a machine after a certain period of use, especially on a filter screen, is very prone to secondary pollution of the purified air. Ultraviolet sterilization is often used in the industry to deal with this problem. However, it is easy to cause the light aging of internal components of the machine, thereby affecting the life of the whole machine and reducing the user experience. Meanwhile, the separate design of sterilization and filtration devices reduces a working efficiency, and a structure of an air purifier is more complex.

SUMMARY

1. Technical Problem to be Solved

In view of the above defects in the art known to inventors, some embodiments of the present disclosure provide a novel disinfection purifier. The problems that purifiers known to inventors are very prone to secondary pollution of purified air and ultraviolet sterilization equipment known to inventors is easy to age and has a poor sterilization effect. Meanwhile, the problems that filter disinfection devices known to inventors have a complex structure, sterilization and filtration devices are designed separately and the working efficiency of filter disinfection is low are also solved.

2. Technical Solution

To solve the above technical problem, some embodiments of the present disclosure provide a novel disinfection purifier. The novel disinfection purifier includes: a purifier housing, and a purification device body and an air suction device disposed inside the purifier housing. Air passes through the purification device body by means of the air suction device and is sterilized.

An air inlet is provided on a side wall of the purifier housing, or an air inlet is provided on a bottom of the purifier housing, or an air inlet is provided on a side wall of the purifier housing and a bottom of the purifier housing, and an air outlet is provided on a top of the purifier housing.

The purification device body includes a disinfection portion and a filter portion sleeving an outside of the disinfection portion. External air enters the disinfection portion after being filtered by the filter portion under a suction of the air suction device and flows out from an upper part of the disinfection portion.

The novel disinfection purifier includes a plurality of ultraviolet light sources disposed in the disinfection portion. A lamp holder is disposed at an end of the ultraviolet light source of the plurality of ultraviolet light sources.

The purification device body further includes a mounting base and an upper fixing seat correspondingly fitted. The mounting base is provided with a lamp holder fixing portion and a filter clamping portion. The lamp holder fixing portion is located on an inner ring of the mounting base. The filter clamping portion is located on an outer ring of the mounting base. The filter portion is mounted in fit with the upper fixing seat through the filter clamping portion.

A fixing bracket is disposed between the mounting base and the upper fixing seat. A fixing rod is penetrated through a middle of the fixing bracket. Two ends of the fixing rod are connected and fixed with the mounting base and the upper fixing seat respectively. The fixing bracket is abutted against the lamp holder at an upper end of an ultraviolet light source.

A filter base is disposed at a bottom of the filter portion. The filter base is rotatably clamped and fixed with the filter clamping portion, so as to fix the filter portion to the filter clamping portion.

The mounting base is a sealing structure. A power terminal is disposed at a side of the mounting base. The power terminal supplies power to the ultraviolet light source.

A clamping protrusion is disposed on a side wall of the lamp holder at a lower end of the ultraviolet light source. The lamp holder may be clamped to a lamp holder clamping groove on the lamp holder fixing portion through the clamping protrusion.

The fixing bracket include a plurality of supporting ribbed plates, the plurality of supporting ribbed plates are disposed on a side wall of the fixing bracket. An upper part of the supporting ribbed plate is abutted against the lamp holder at the upper end of the ultraviolet light source. A positioning protrusion is disposed on a lower part of the supporting ribbed plate. The positioning protrusion is correspondingly fitted to a positioning hole provided on the mounting base.

The ultraviolet light source includes four ultraviolet light tubes. Four lamp holders at upper ends of the four ultraviolet light tubes are integrally disposed in a cross shape. An upper end of the fixing rod passes through a central position of the four lamp holders and is connected with the upper fixing seat.

The purification device body further includes a mounting base correspondingly fitted. The mounting base is provided with a lamp holder fixing portion and a filter clamping portion. The lamp holder fixing portion is located on an inner ring of the mounting base. The filter clamping portion is located on an outer ring of the mounting base. The filter portion is mounted through the filter clamping portion.

A filter base is disposed at a bottom of the filter portion. The filter base is rotatably clamped and fixed with the filter clamping portion, so as to fix the filter portion to the filter clamping portion.

The mounting base is a sealing structure. A power terminal is disposed at a side of the mounting base. The power terminal supplies power to the ultraviolet light source.

The ultraviolet light source includes at least two ultraviolet light tubes. The ultraviolet light tubes are inserted and fixed to the lamp holder fixing portion through a lamp holder located at one end of the ultraviolet light source. The lamp holder is covered and fixed by a lamp holder cover.

The air suction device is located on an upper part of the purification device body. The air suction device includes a supporting frame, and a fan and a motor fixed within the supporting frame. The novel disinfection purifier include a light shading device, the light shading device is disposed between the air suction device and the purification device body.

The light shading device includes a plurality of conical baffles sleeved at intervals from inside to outside.

The purifier housing includes four supporting columns located at top corners of the purifier housing, a plurality of housing plates, a housing base, and a housing top cover. The supporting columns fix the housing top cover, the air suction device, the purification device body, and the housing base successively from top to bottom. The housing plates are fixed by the supporting columns and form an outer wall of the purifier housing.

The novel disinfection purifier further includes: a control device and a detection device. The control device is disposed on an upper part of the housing top cover. The detection device is disposed on the housing plate. The control device includes a display panel and a control knob. The detection device includes a detection mounting cover plate and an air quality sensor. The housing top cover is further provided with a dustproof hood.

The filter portion includes a barrel-shaped HEPA filter screen.

Each of the four lamp holders at the upper ends of the four ultraviolet lamp tubes is provided with a lamp holder hoop for fixing a corresponding lamp tube. Two ends of the lamp holder hoop are provided with protruding buckles. Two sides of the lamp holder are provided with clamping buckle plates corresponding to the buckles. The lamp holder hoop is fixed to the lamp holder through a fit of the buckles and the clamping buckle plates.

3. Beneficial Effect

Compared with the art known to inventors, the novel disinfection purifier of the present disclosure achieves the effect of sterilizing air by means of a sterilization device. Specifically, on the one hand, by means of a filter portion, accelerated structure aging of the purifier caused by ultraviolet rays is effectively prevented, it is also ensured that the ultraviolet rays do not leak, and thus the device is safer to use.

On the other hand, the barrel-shaped filter portion completely wraps the sterilization portion, and filtration and disinfection are integrated into an overall device through a corresponding fixing structure, thereby greatly improving the overall working efficiency. Meanwhile, the filter portion can be simply disassembled by rotating, and can be easily replaced after a long time of use.

Further, by means of a conical baffle, the escape of ultraviolet light can be well blocked while an air outlet effect is not affected. That is, light of ultraviolet lamp tubes cannot see from the whole device when viewed from the upper part. By means of the control device and the detection device, while realizing the operation control of the purifier, an overall environmental condition is detected and displayed through a display panel. By optimizing the overall structure, a desktop-type miniaturized structural design is realized.

The ultraviolet lamp tubes are also fixed by means of lamp holder hoops, so as to prevent the ultraviolet lamp tubes from rotating and falling off.

Figure 1:
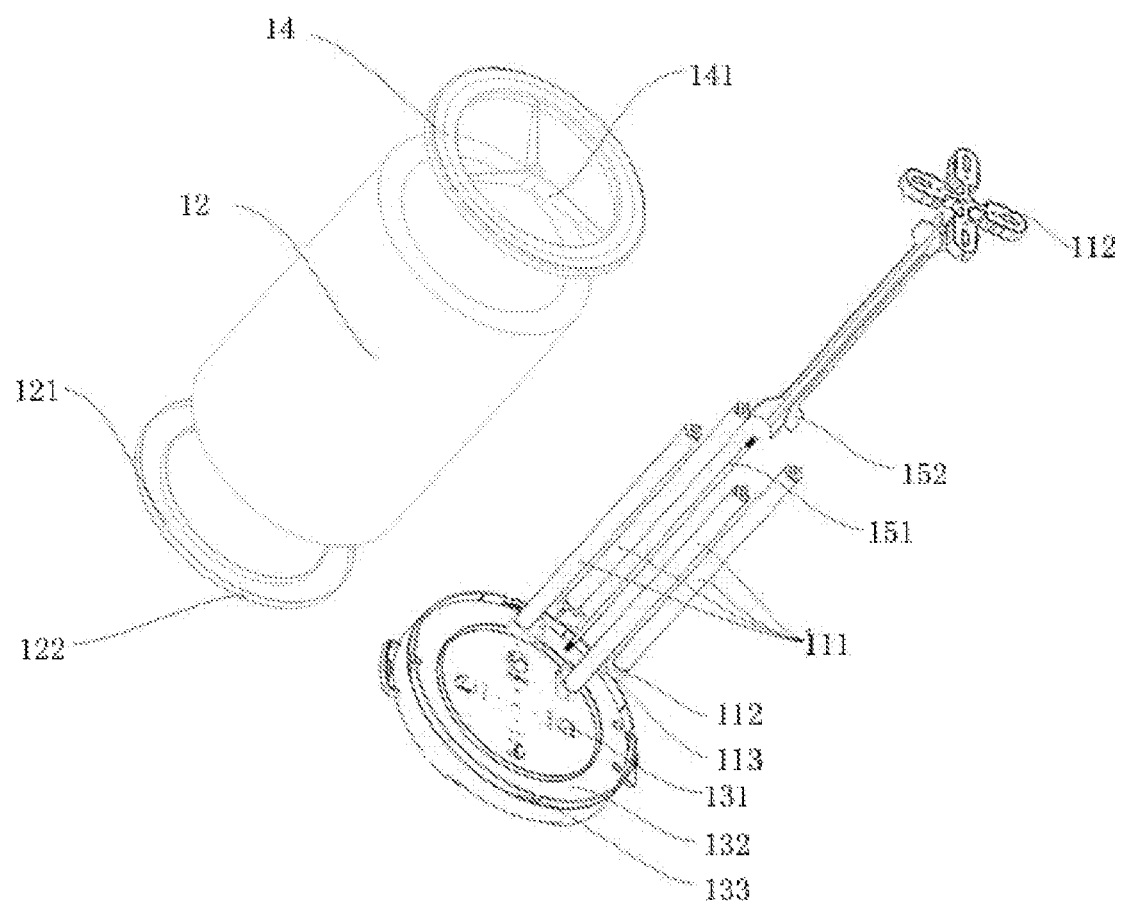
FIG. 1 illustrates an exploded view of a purification device body according to Embodiment 1 of the present disclosure.
Figure 2:
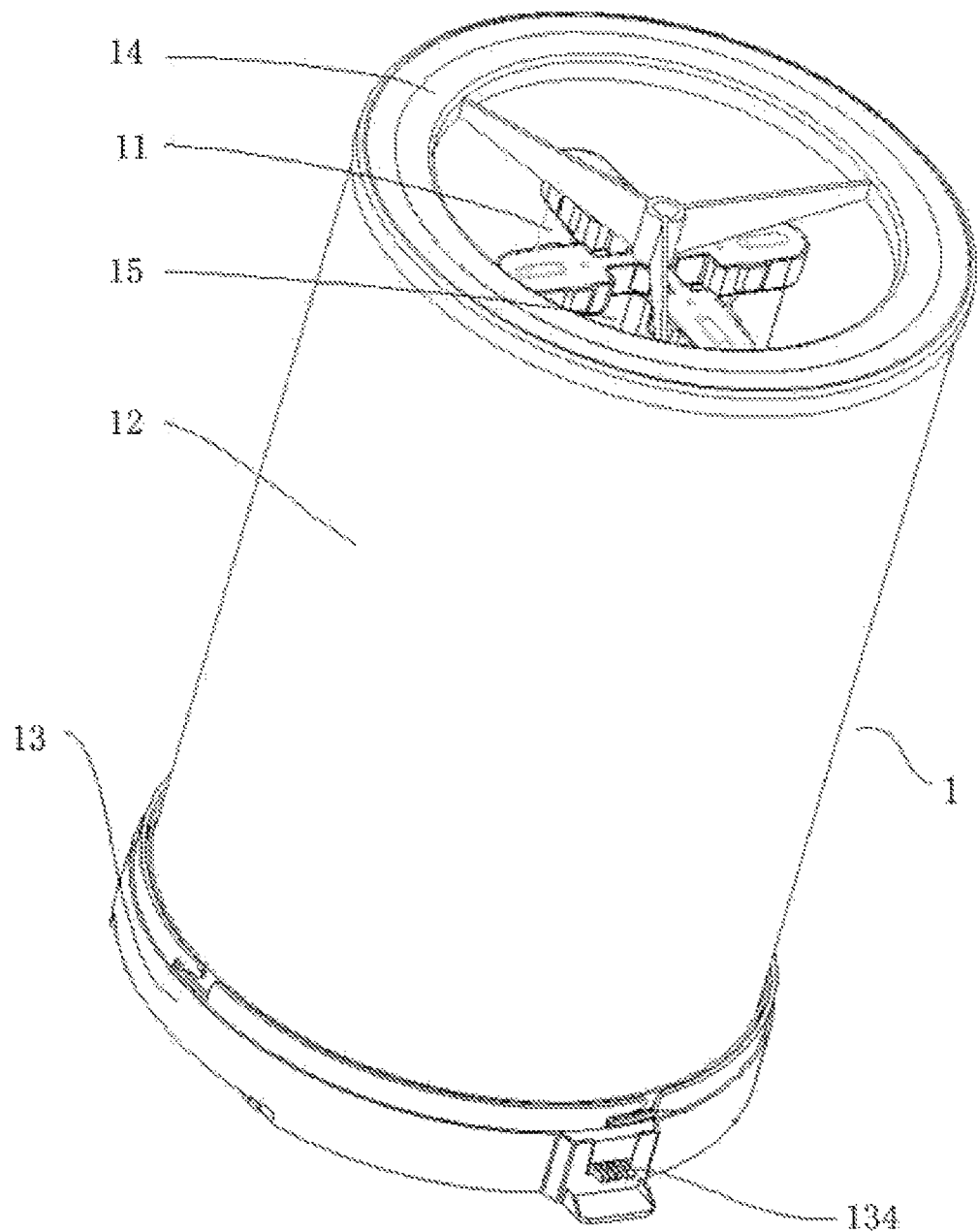
FIG. 2 illustrates a three-dimensional view of a purification device body according to Embodiment 1 of the present disclosure.

1: purification device body;
11: disinfection portion; 12: filter portion; 13: mounting base; 14: upper fixing seat; 15: fixing bracket;
111: ultraviolet light source; 112: lamp holder; 113: clamping protrusion; 1121: lamp holder cover; 1122: lamp holder hoop; 1123: buckle; 1124: clamping buckle plate; 121: filter portion base; 122: clamping pin; 131: lamp holder fixing portion; 132: filter clamping portion; 133: clamping groove; 134: power terminal; 141: connecting rod; 151: fixing rod; 152: supporting ribbed plate; 153: positioning protrusion;
2: air suction device;
21: supporting frame; 22: fan; 23: motor;
3: light shading device;
31: conical baffle;
4: control device;
41: display panel; 42: control knob;
5: detection device;
51: detection mounting cover plate; 52: air detection sensor;
6: micro-switch;
61: push rod; and 62: locking fastener.

DETAILED DESCRIPTION OF THE EMBODIMENTS

Specific embodiments of the present disclosure will be described below in further detail with reference to the drawings and embodiments. The following embodiments serve to illustrate the present disclosure but are not intended to limit the scope thereof.

Embodiment 1

Some embodiments of the present disclosure provide a novel disinfection purifier. As shown in FIGS. 1-13, the novel disinfection purifier includes: a purifier housing 100, and a purification device body 1 and an air suction device 2 disposed inside the purifier housing 100. Air passes through the purification device body 1 by means of the air suction device 2 and is sterilized. An air inlet 101 is provided on a side wall of the purifier housing, or an air inlet is provided on a bottom of the purifier housing 100, or an air inlet is provided on a side wall of the purifier housing and a bottom of the purifier housing, and an air outlet 102 is provided on a top of the purifier housing 100. The air inlet 101 is provided near the filter portion 12.

The purification device body 1 includes a disinfection portion 11 and a filter portion 12 sleeving an outside of the disinfection portion 11. External air enters the disinfection portion 11 after being filtered by the filter portion 12 under the suction of the air suction device 2. In this embodiment, the novel disinfection purifier include a plurality of ultraviolet light sources 111 disposed in the disinfection portion 11. Ultraviolet rays are used as a main method for disinfection and sterilization. The filter portion 12 includes a barrel-shaped HEPA filter screen. In this embodiment, the filter portion 12 is cylindrical, square or in other shapes according to usage requirements. The disinfection portion 11 is completely wrapped by the surrounding filter portion 12, so that an integrated filtration and disinfection device is formed. The side wall of the filter portion 12 is used as an air inlet position. That is, when external air enters the disinfection portion 11, the air is effectively filtered by the filter portion 12, so that the air inlet area and the filtering efficiency are greatly increased, thereby improving the working efficiency of the novel disinfection purifier of this embodiment.

As shown in FIG. 1, the purification device body 1 further includes a mounting base 13 and an upper fixing seat 14 correspondingly fitted. The upper fixing seat 14 is of a hollowed-out design. A middle structure is connected with an edge structure through three connecting rods 141. The mounting base 13 is provided with a lamp holder fixing portion 131 and a filter clamping portion 132. Moreover, a clamping protrusion 113 is disposed on a side wall of the lamp holder 112 at a lower end of the ultraviolet light source 111. The lamp holder is clamped to a lamp holder clamping groove on the lamp holder fixing portion 131 through the clamping protrusion 113. The lamp holder fixing portion 131 is located on an inner ring of the mounting base 13. The filter clamping portion 132 is located on an outer ring of the mounting base 13. Both upper and lower ends of the ultraviolet light source 111 are provided with lamp holders 112. The ultraviolet light source 111 is fixed to the mounting base 13 and the upper fixing seat 14 through the lamp holders 112. In this embodiment, there are four ultraviolet light sources 111. The quantity of the ultraviolet light sources 111 is set according to usage requirements.

The filter portion 12 is fitted and fixed to the upper fixing seat 14 through the filter clamping portion 132. In this embodiment, a filter base 121 is disposed at a bottom of the filter portion 12. The filter base 121 is rotatably clamped and fixed to the filter clamping portion 132, so as to fix the filter portion 12 to the filter clamping portion 132. The filter base 121 and the filter clamping portion 132 are provided with rotary clamping devices fitted to each other. In this embodiment, at least two clamping grooves 133 are provided on the side wall of the filter clamping portion 132. Corresponding clamping pins 122 are disposed on the filter base 121. When the filter portion 12 is used for a long period of time, the filtration and ventilation capacities are affected, and the filter portion needs to be replaced at regular intervals. By including the above design, when it is necessary to replace the filter portion 12, the filter portion 12 can be conveniently replaced by screwing.

In this embodiment, the mounting base 13 is designed as a sealing structure. External air flows out from an upper part of the disinfection portion 11. Moreover, a power terminal 134 is disposed at a side of the mounting base 13. The power terminal 134 supplies power to the ultraviolet light source 111.

Figure 20:
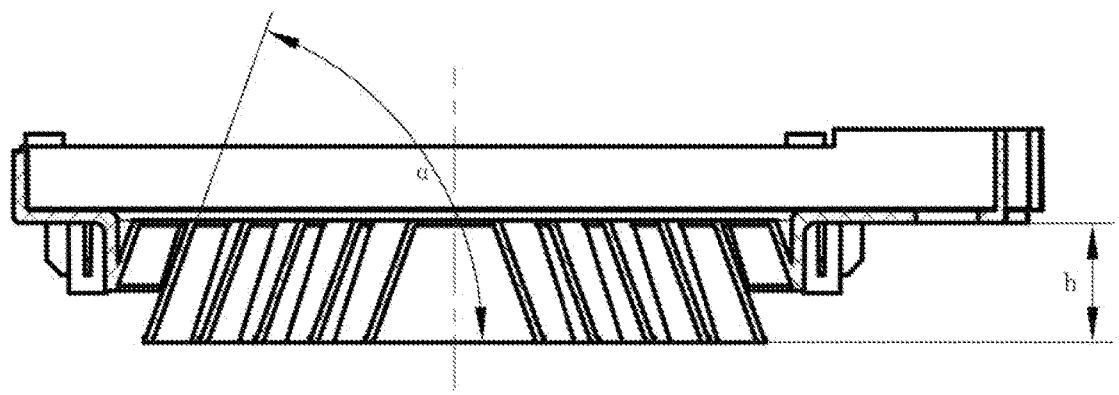
FIG. 20 illustrates a cross-sectional view 1 of a light shading device according to Embodiment 1 of the present disclosure.
Figure 21:
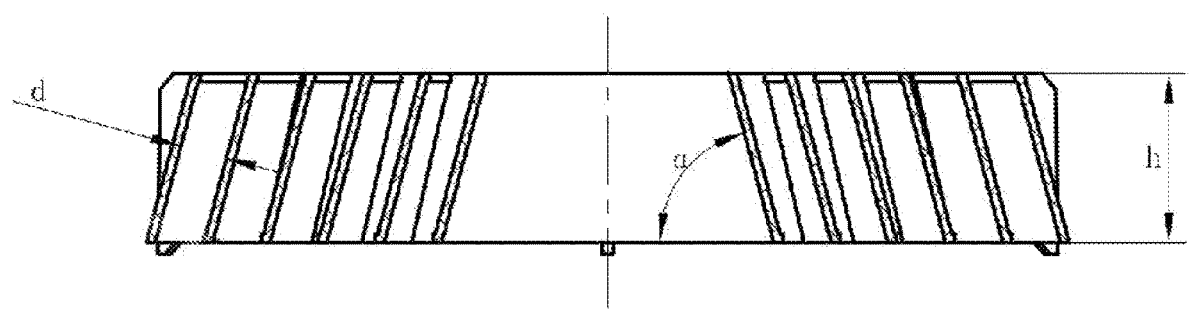
FIG. 21 illustrates a cross-sectional view 2 of the light shading device according to Embodiment 1 of the present disclosure.

As shown in FIGS. 6-13, with regard to the arrangement of other structures of the purifier, the air suction device 2 is located on an upper part of the purification device body 1. The air suction device 2 includes a supporting frame 21, and a fan 22 and a motor 23 fixed within the supporting frame 21. A light shading device 3 is further disposed between the air suction device 2 and the purification device body 1. Specifically, the light shading device 3 includes a plurality of conical baffles 31 sleeved at intervals from inside to outside. An air passage is disposed between every two conical baffles 31. By means of the conical baffles 31, the escape of ultraviolet light can be well blocked while an air outlet effect is not affected. That is, light of the ultraviolet lamp tubes is not seen from the whole device when viewed from the upper part. As shown in the cross-sectional views of the light shading device 3 in FIGS. 20 and 21, a height of the conical baffle 31 is h, an included angle between a conical surface of the conical baffle 31 and a bottom plane is α, and an interval between the conical baffles 31 is d. For different models and sizes of purifiers, in order to achieve the best light shading and air guiding effects, 20 mm≤h≤35 mm, 8 mm≤d≤9 mm, 70°≤α≤80°. In this embodiment, due to the requirements for purifying two large spaces, the height of the conical baffle 31 is 30 mm, the interval d between the conical baffles 31 is 8.3 mm, and the included angle α between the conical surface of the conical baffle 31 and the bottom plane is 75°.

Figure 8:
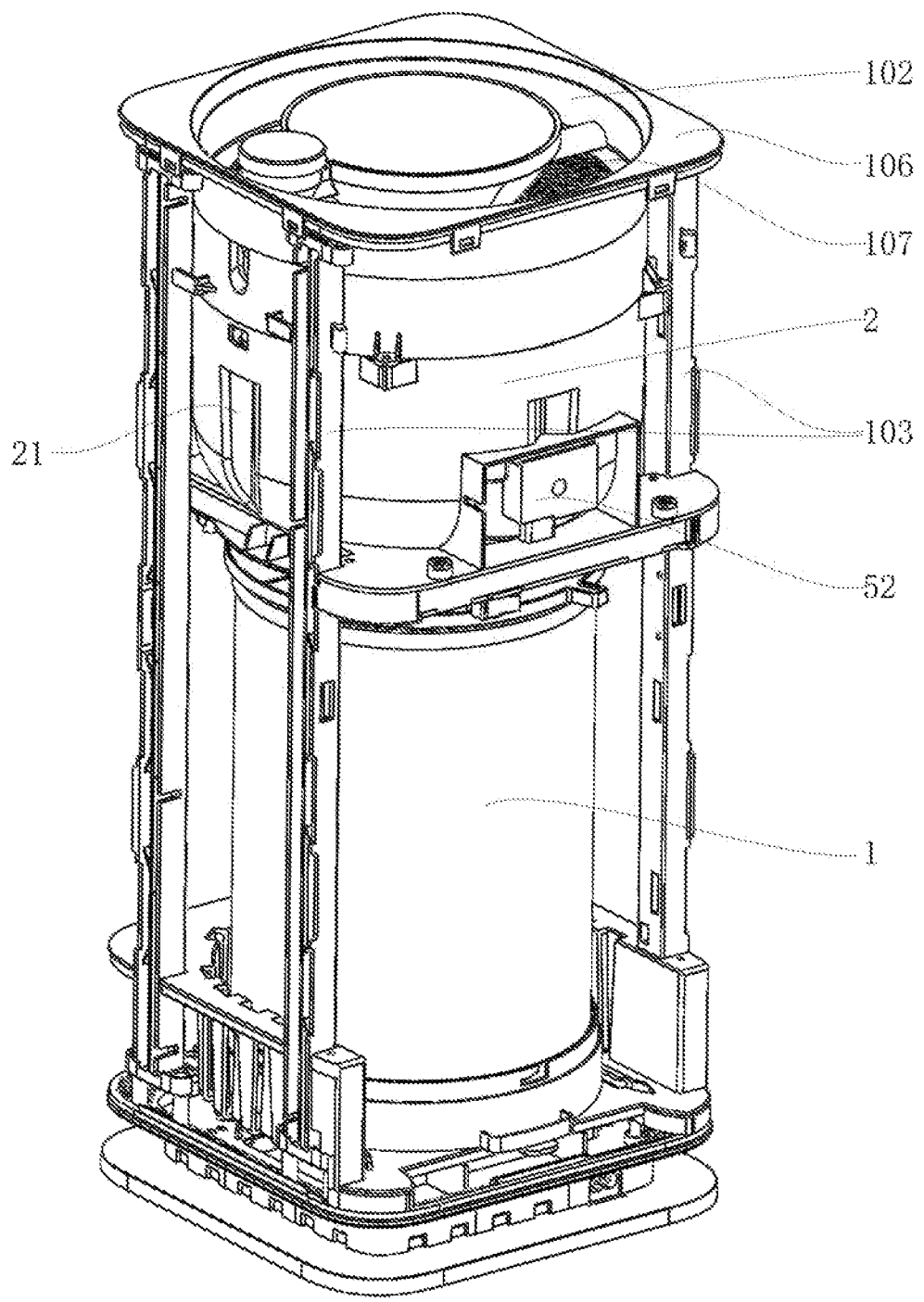
FIG. 8 illustrates a three-dimensional view 3 of the purifier according to Embodiment 1 of the present disclosure.
Figure 9:
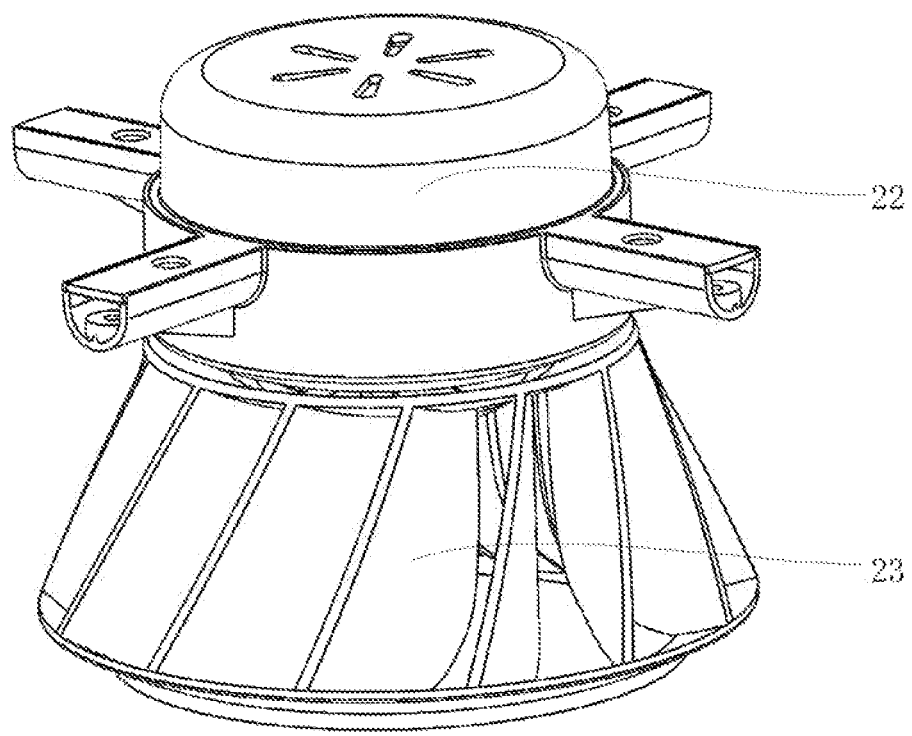
FIG. 9 illustrates an internal structure view of an air suction device according to Embodiment 1 of the present disclosure.
Figure 10:
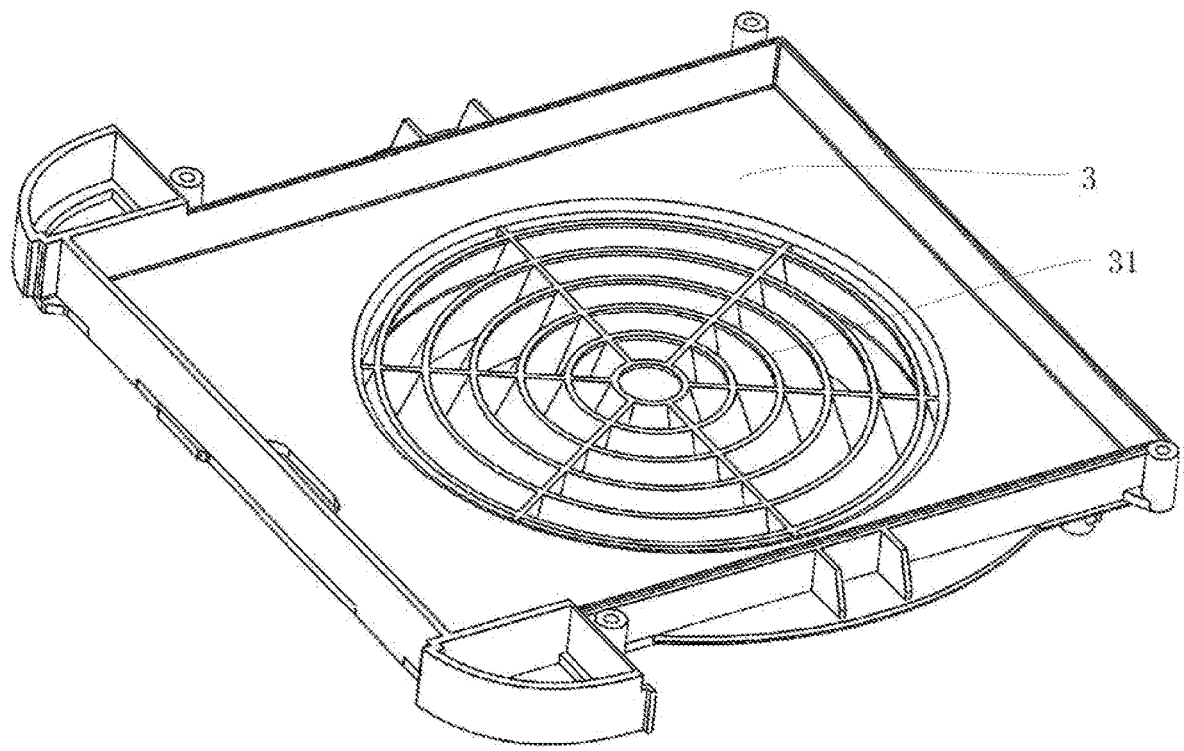
FIG. 10 illustrates a structure view of a light shading device according to Embodiment 1 of the present disclosure.
Figure 11:
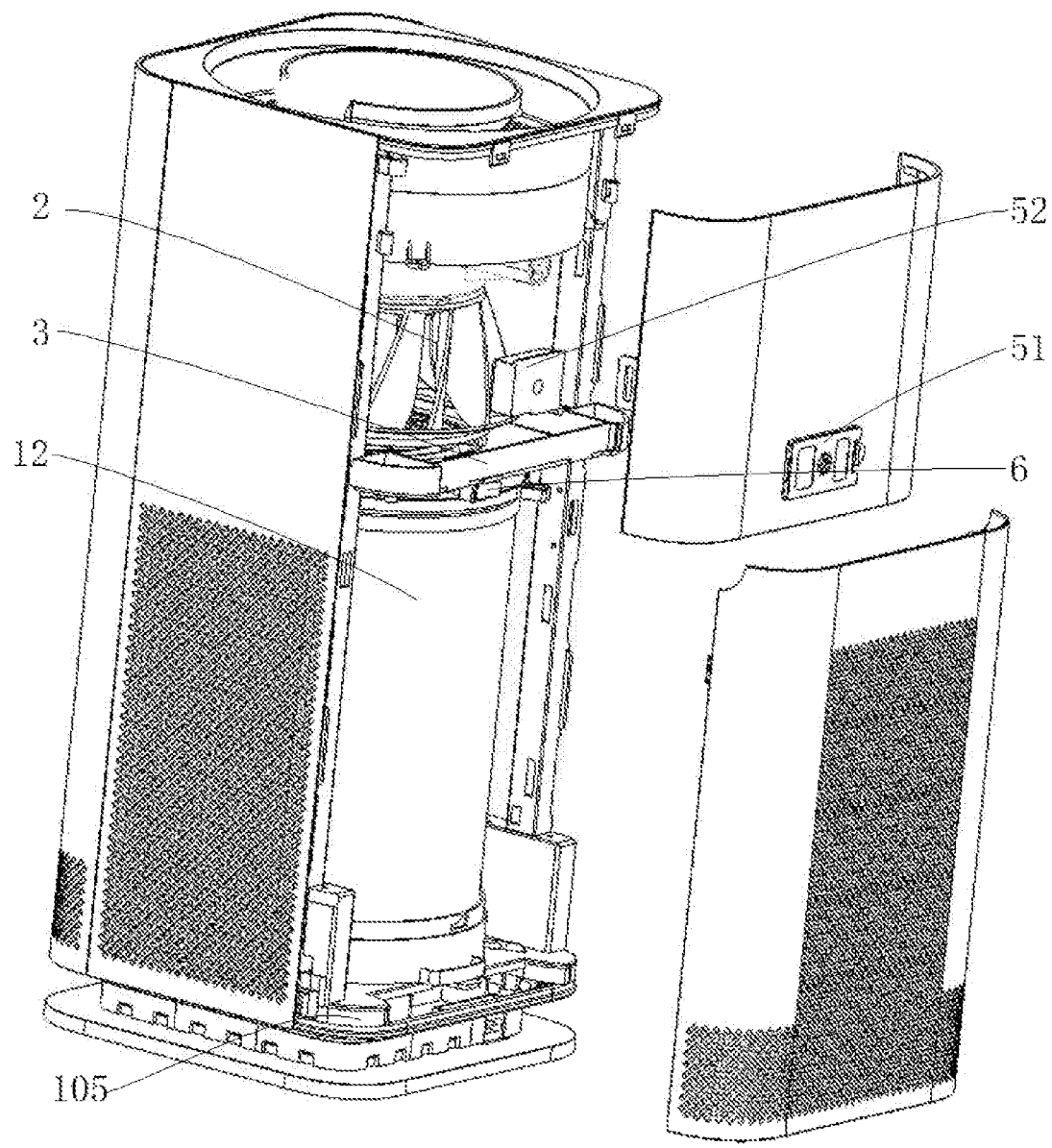
FIG. 11 illustrates a three-dimensional view 4 of a purifier according to Embodiment 1 of the present disclosure.
Figure 12:
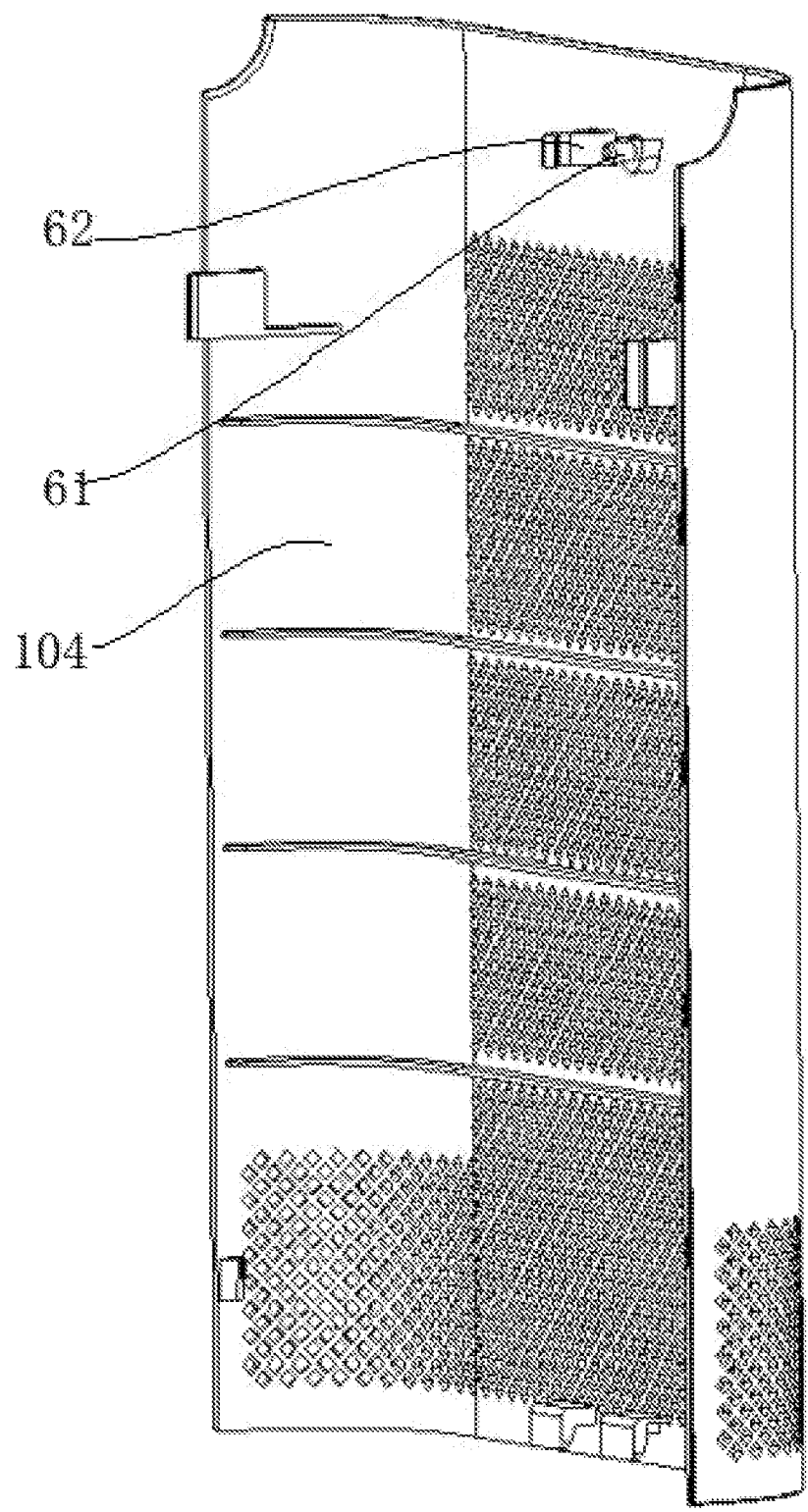
FIG. 12 illustrates a three-dimensional view of a housing plate at one side according to Embodiment 1 of the present disclosure.
Figure 13:
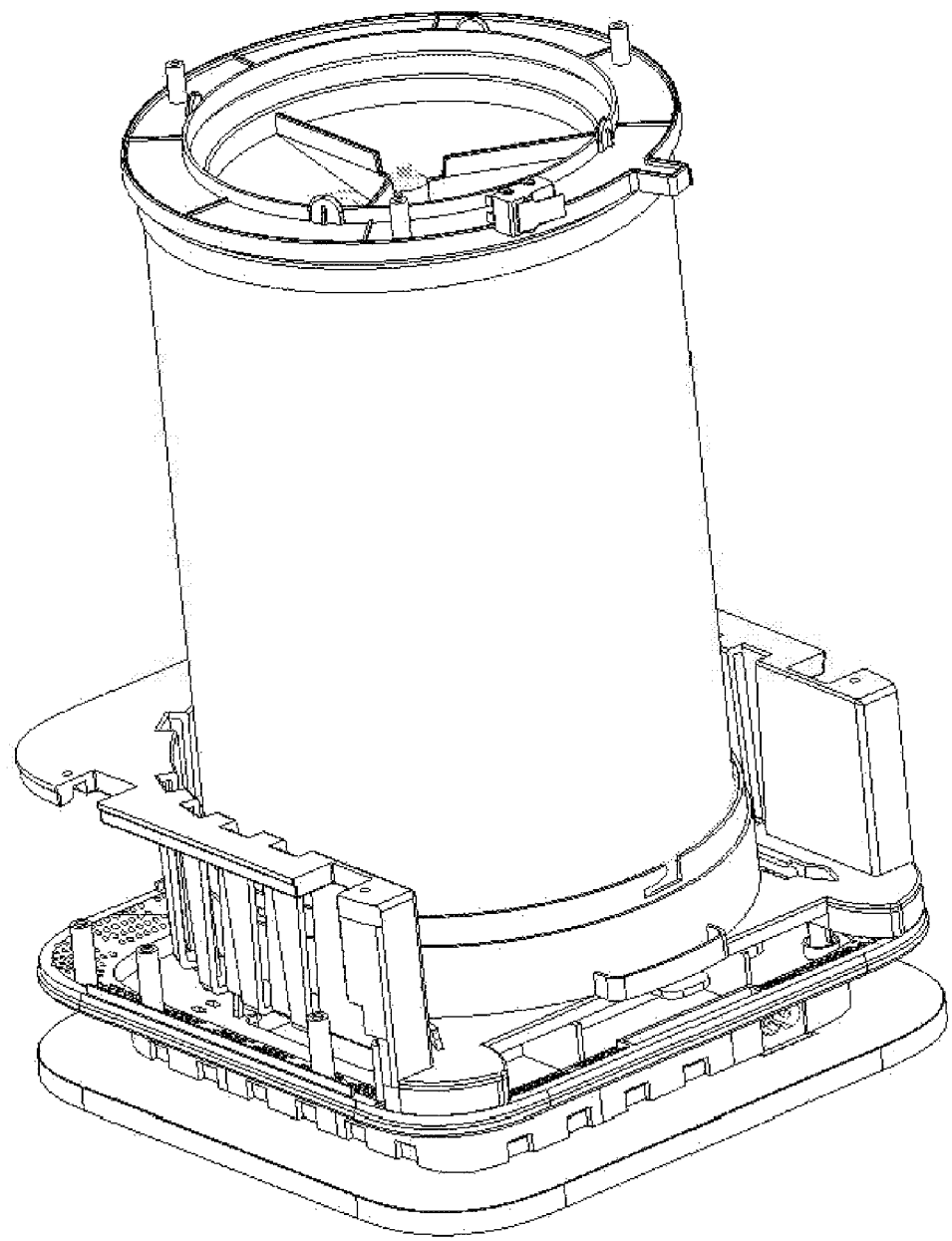
FIG. 13 illustrates a structure view of a disinfection portion and a housing base according to Embodiment 1 of the present disclosure.
Figure 14:
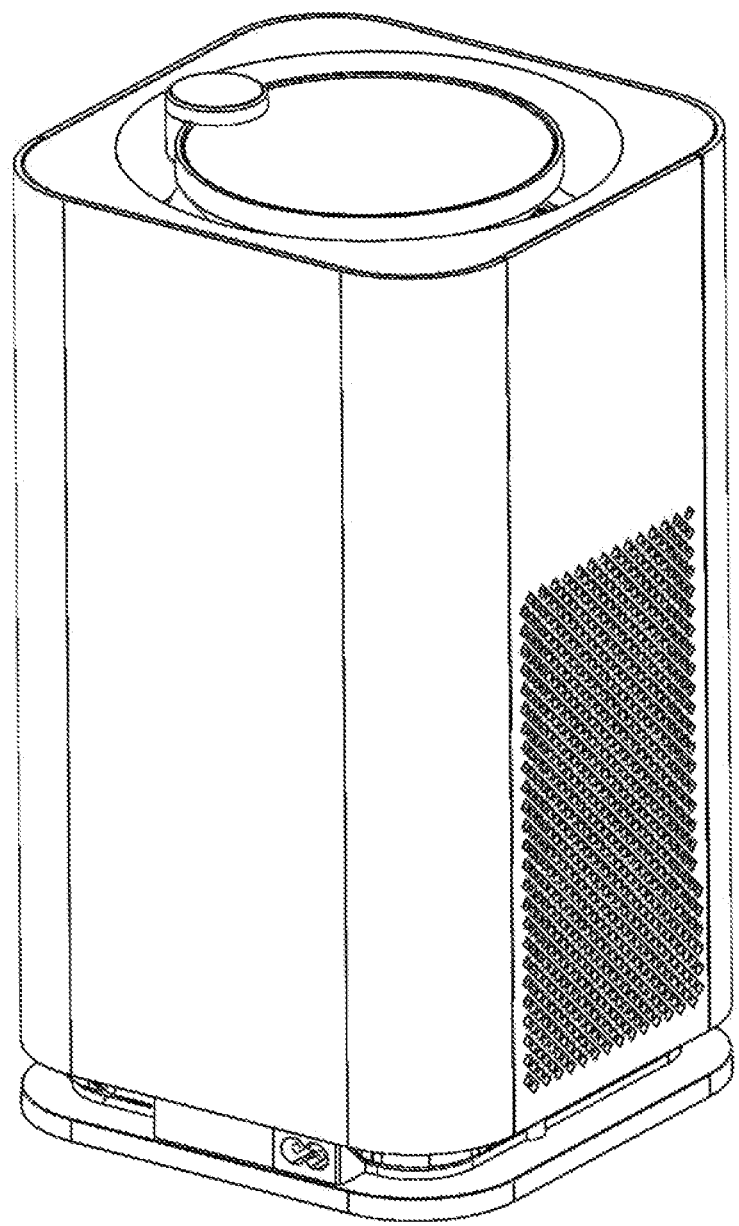
FIG. 14 illustrates a three-dimensional view of a purifier according to Embodiment 4 of the present disclosure.
Figure 15:
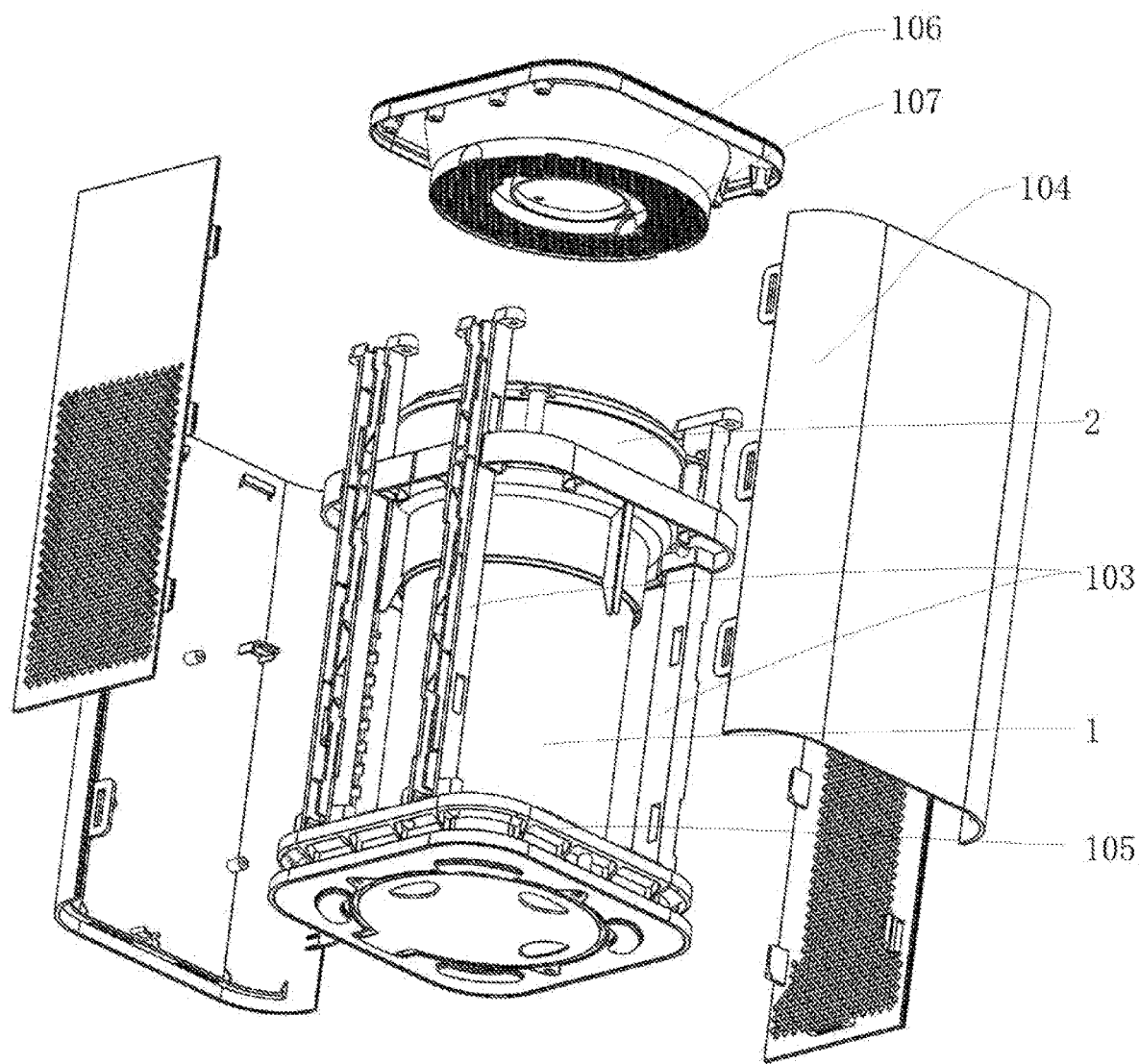
FIG. 15 illustrates an exploded view of the purifier according to Embodiment 4 of the present disclosure.
Figure 16:
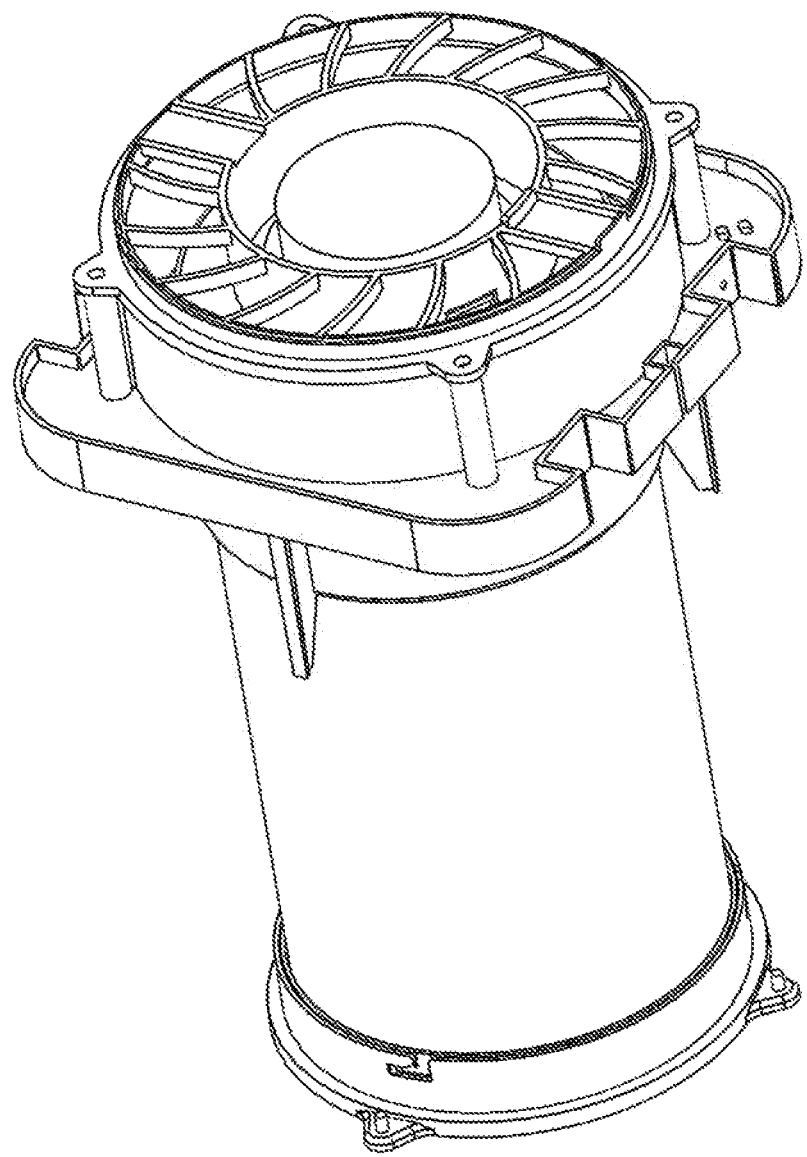
FIG. 16 illustrates a three-dimensional view of a purification device body and an air suction device according to Embodiment 4 of the present disclosure.

As shown in FIG. 8, the purifier housing 100 includes four supporting columns 103 located at top corners of the purifier housing, a plurality of housing plates 104, a housing base 105, and a housing top cover 106. The supporting columns 103 fix the housing top cover 106, the air suction device 2, the purification device body 1, and the housing base 105 successively from top to bottom. The housing plates 104 are fixed by the supporting columns 103 and form an outer wall of the purifier housing 100. The overall structure is firm and reliable, and the mounting is convenient. The filter portion 12 is easily disassembled and replaced.

In this embodiment, the purifier further includes: a control device 4 and a detection device 5. The control device 4 is disposed on an upper part of the housing top cover 106. The detection device 5 is disposed on the housing plate 104. The control device 4 includes a display panel 41 and a control knob 42. The detection device 5 includes a detection mounting cover plate 51 and an air quality sensor 52. In this embodiments, the air quality sensor 52 is configured to detect the air quality of current environment, such as PM2.5 and values of ambient temperature and humidity, which is displayed through the display panel 41. The control knob 42 can set the functions of wind speed, the illumination intensity of the ultraviolet lamp tubes, timing setting, etc. The housing top cover 106 is further provided with a dustproof hood 107, so as to prevent external foreign matters and dust from entering the device.

A micro-switch 6 is disposed at one side of the housing plate. The housing plate at this side is detachable. In this embodiments, a push rod 61 and a locking fastener 62 are disposed on an inner wall of the housing plate. After the cover is closed, the micro-switch is pushed to be turned on by the push rod 61 to turn on a circuit. The ultraviolet light sources 111 in the disinfection portion 11 can work normally. If the cover is not normally closed, the ultraviolet light sources cannot work normally. When the filter portion 12 is replaced or disassembled, the housing plate is opened, and the purifier stops working, which can improve the safety of the usage process.

Embodiment 2

Compared with Embodiment 1, as shown in FIG. 1, in this embodiment, a fixing bracket 15 is disposed between the mounting base 13 and the upper fixing seat 14. A fixing rod 151 penetrates through the middle of the fixing bracket 15. Both the mounting base 13 and the upper fixing seat 14 are provided with mounting holes. Two ends of the fixing rod 151 are connected and fixed with the mounting base 13 and the upper fixing seat 14 through the mounting holes respectively, and are specifically fixed by means of threaded connection. The fixing bracket 15 is also connected and fixed with the lamp holder 112 at the upper end of the ultraviolet light source 111.

In this embodiment, the fixing rod 151 serves to connect the mounting base 13 and the upper fixing seat 14, and the fixing bracket 15 sleeves the fixing rod 151. In this embodiment, the ultraviolet light source 111 includes four ultraviolet light tubes. Four lamp holders 112 at the upper ends of the four ultraviolet light tubes are integrally disposed in a cross shape. An upper end of the fixing rod 151 passes through a central position of the four lamp holders 112 and is connected with the upper fixing seat 14. Ultraviolet rays generated by the ultraviolet light tubes form a sterilization region with high ultraviolet radiation intensity, thereby achieving rapid and effective sterilization.

Figure 3:
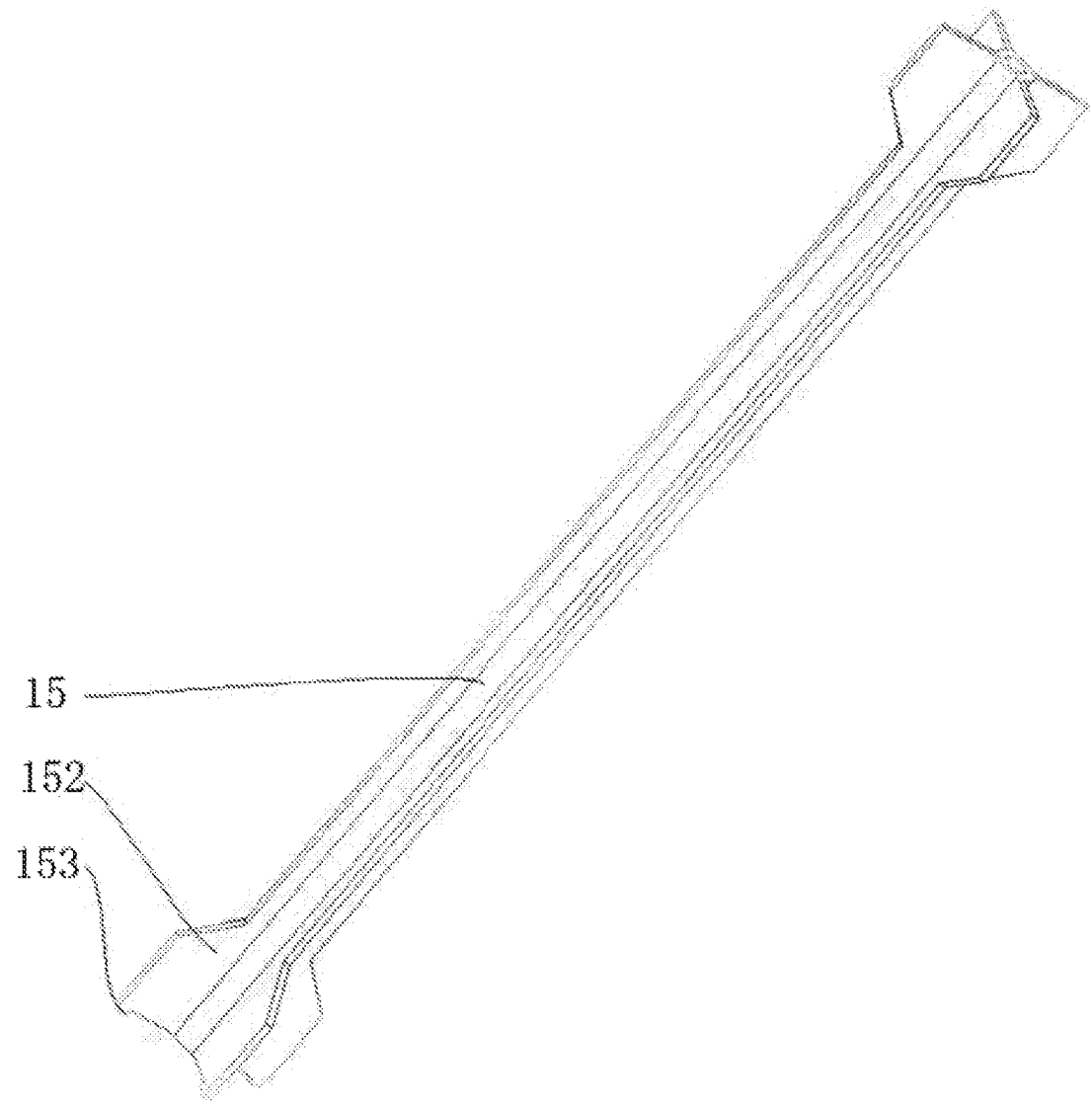
FIG. 3 illustrates a three-dimensional view of a fixing bracket according to Embodiment 1 of the present disclosure.
Figure 4:
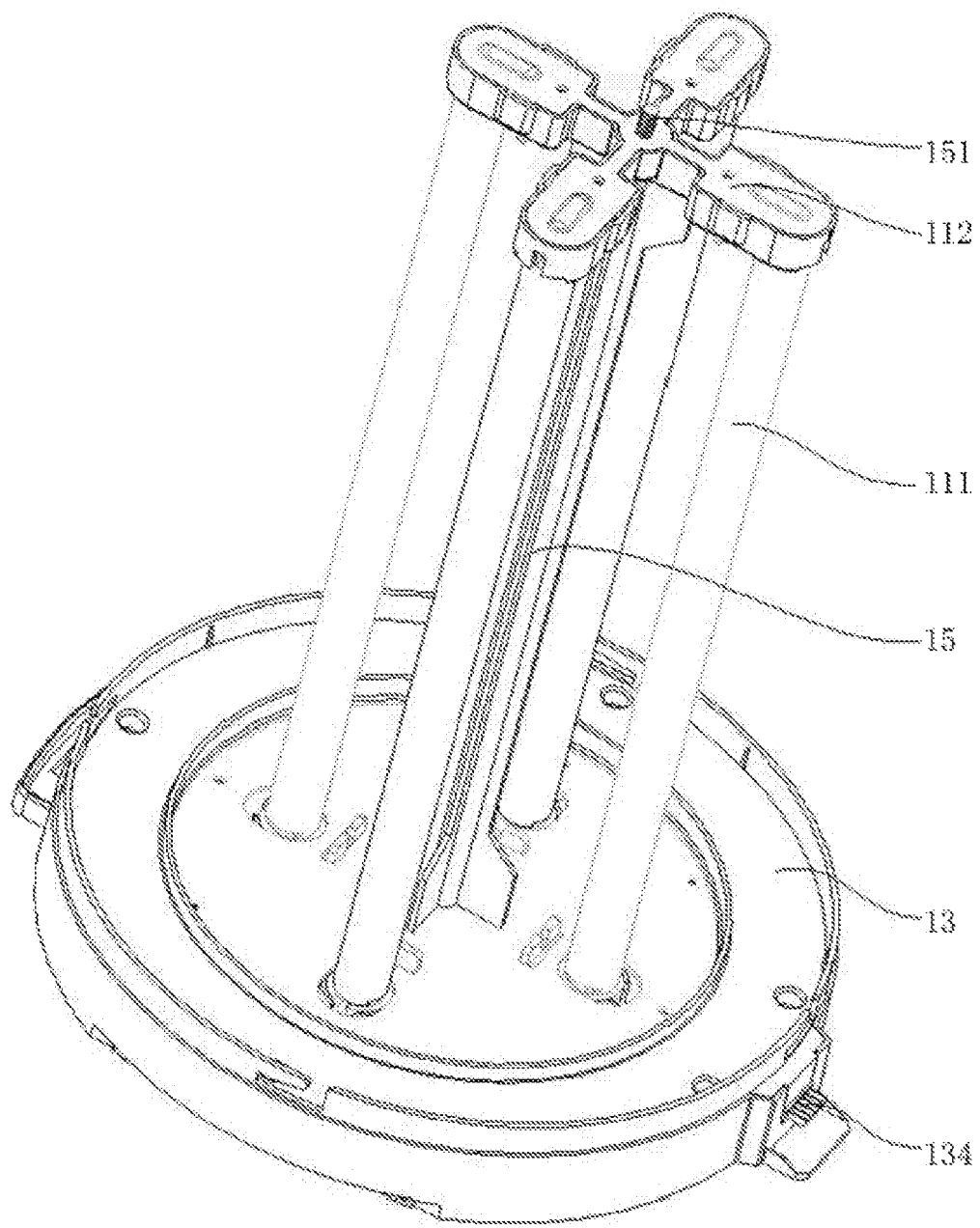
FIG. 4 illustrates an internal structure view of a purification device body according to Embodiment 1 of the present disclosure.

As shown in FIG. 3, four supporting ribbed plates 152 are disposed on a side wall of the fixing bracket 15. An upper part of each supporting ribbed plate 152 is abutted against the corresponding lamp holder 112 at the upper end of the ultraviolet light source 111, so as to achieve a certain supporting function. A positioning protrusion 153 is disposed on a lower part of the supporting ribbed plate 152. The positioning protrusion 153 is correspondingly fitted to a positioning hole provided on the mounting base 13, so as to achieve a positioning effect of preventing the fixing bracket 15 from rotating or changing positions. Meanwhile, the mounting is facilitated, and it is firmer and more reliable to fix.

Embodiment 3

Figure 5:
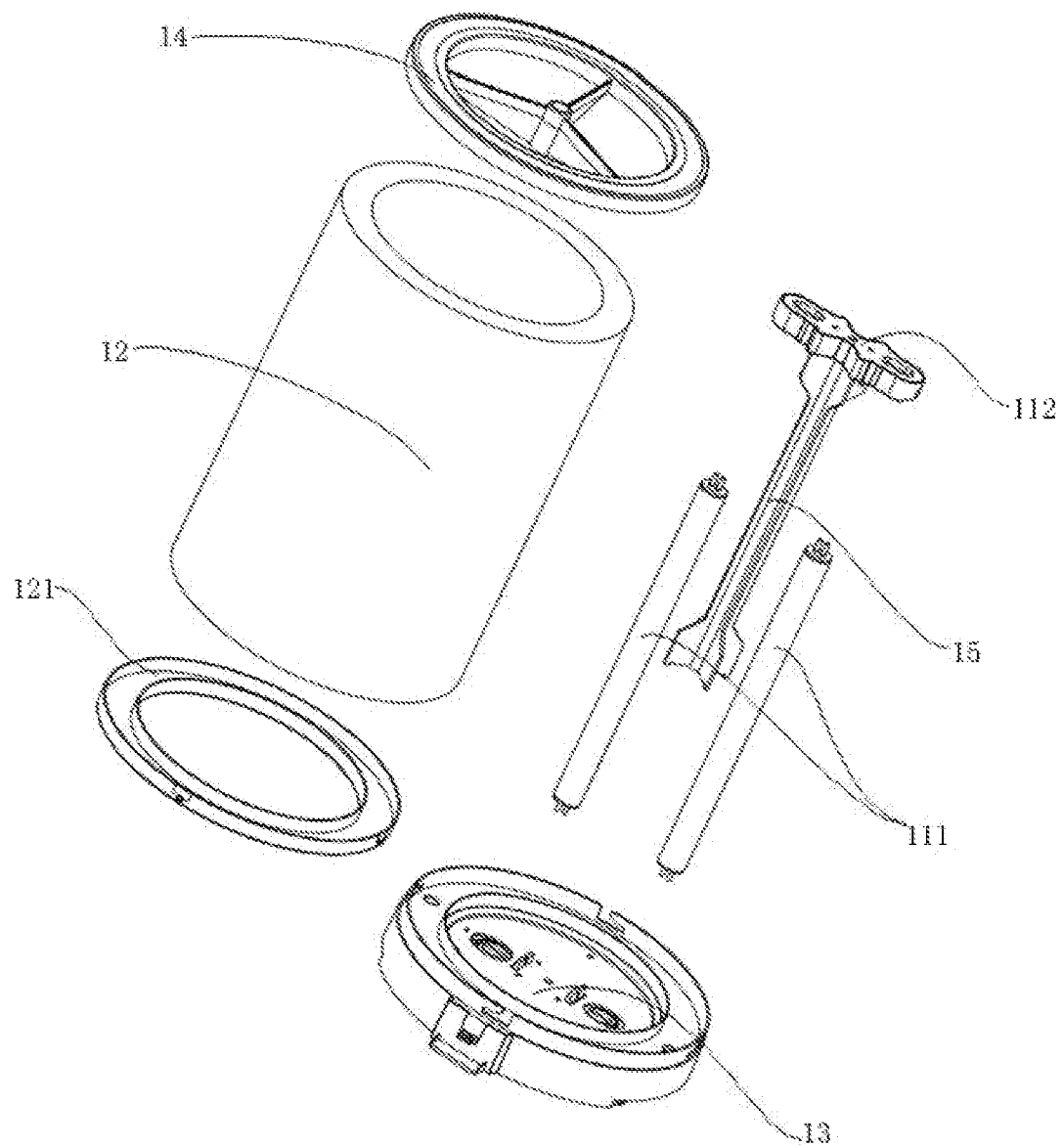
FIG. 5 illustrates an exploded view of Embodiment 3 of the present disclosure.
Figure 6:
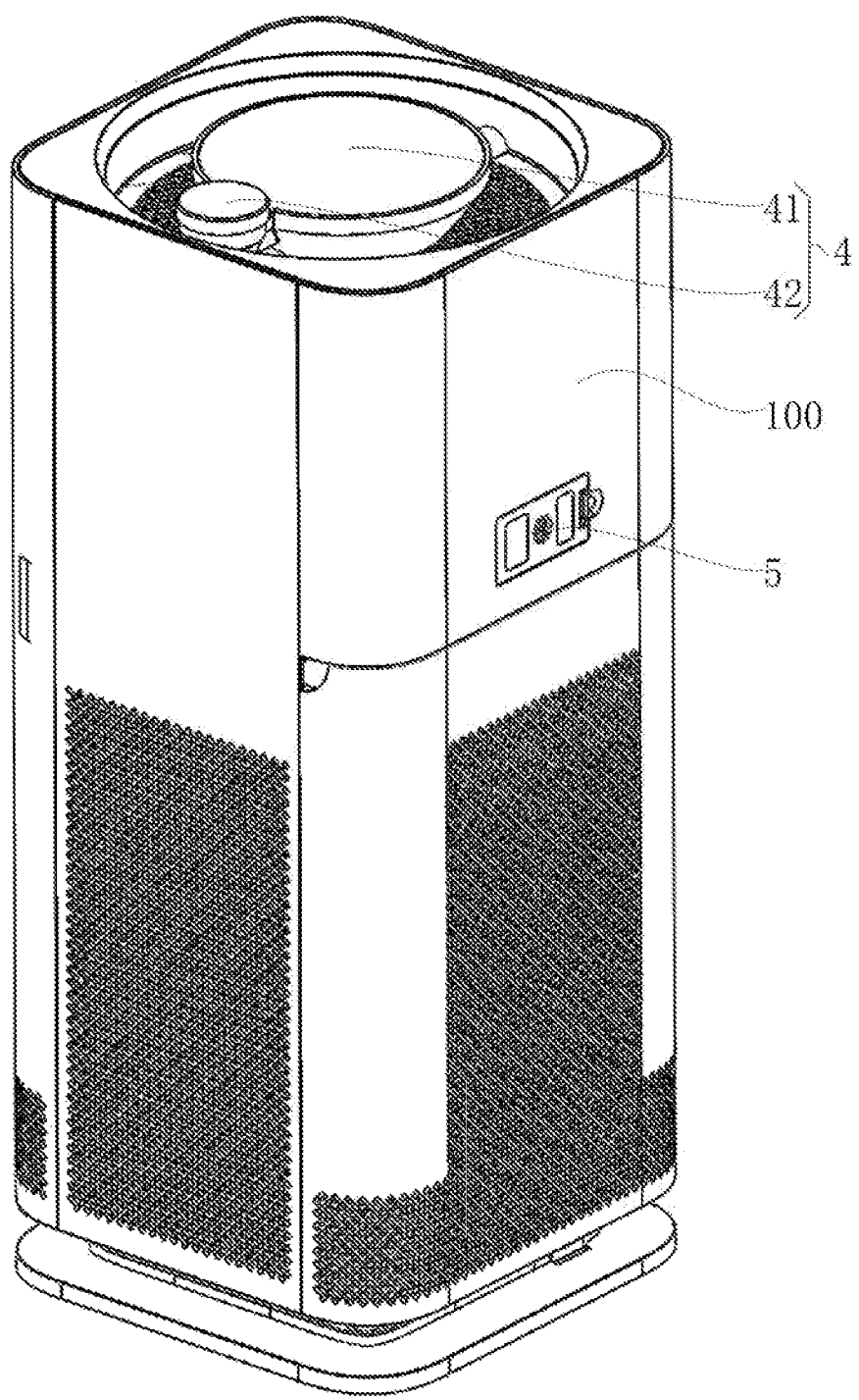
FIG. 6 illustrates a three-dimensional view 1 of a purifier according to Embodiment 1 of the present disclosure.
Figure 7:
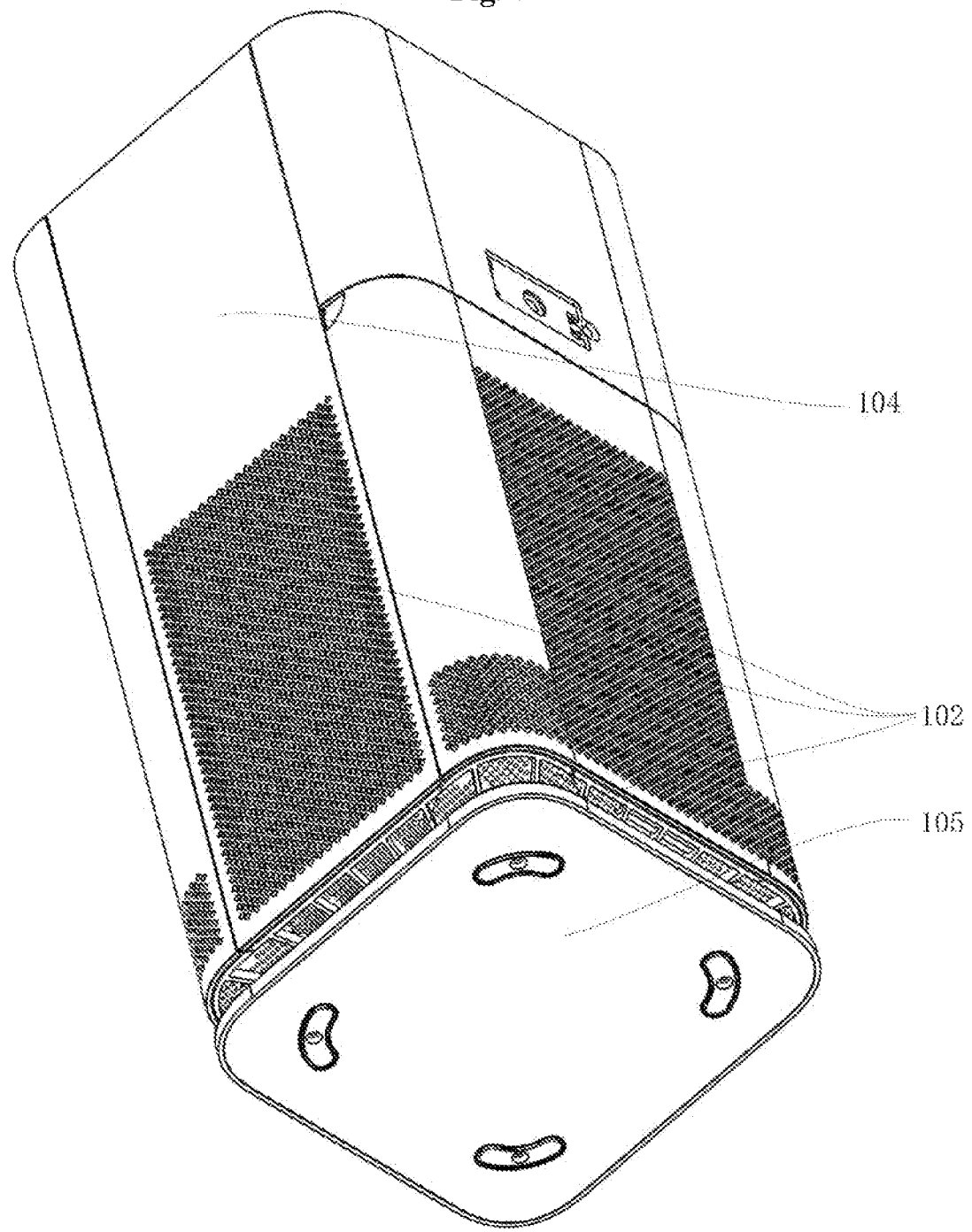
FIG. 7 illustrates a three-dimensional view 2 of the purifier according to Embodiment 1 of the present disclosure.

Compared with Embodiment 2, in this embodiment, as shown in FIG. 5, the ultraviolet light source 111 includes two ultraviolet light tubes. Two lamp holders 112 at the upper ends of the ultraviolet light tubes are integrally disposed in a in-line shape. An upper end of the fixing rod 151 passes through a central position of the two lamp holders 112 and is connected with the upper fixing seat 14.

Embodiment 4

In this embodiment, as shown in FIGS. 14-19, a desktop-type small purifier structure is adopted correspondingly in this embodiment. Therefore, the overall structure is more compact and the overall volume is also smaller. Compared with Embodiment 1, specific differences lie in that the ultraviolet light source 111 includes two ultraviolet light tubes. The ultraviolet light tubes are inserted and fixed to the lamp holder fixing portion 131 through lamp holders 112 located at one end, and the lamp holders 112 are covered and fixed by lamp holder covers 1121. That is, it is unnecessary to power and fix two ends of the ultraviolet lamp tubes at the same time. A fixing structure with one-end insertion is adopted, and the upper fixing seat 14 and the fixing bracket 15 adopted in Embodiment 1 are both omitted directly, thereby saving space.

Figure 17:
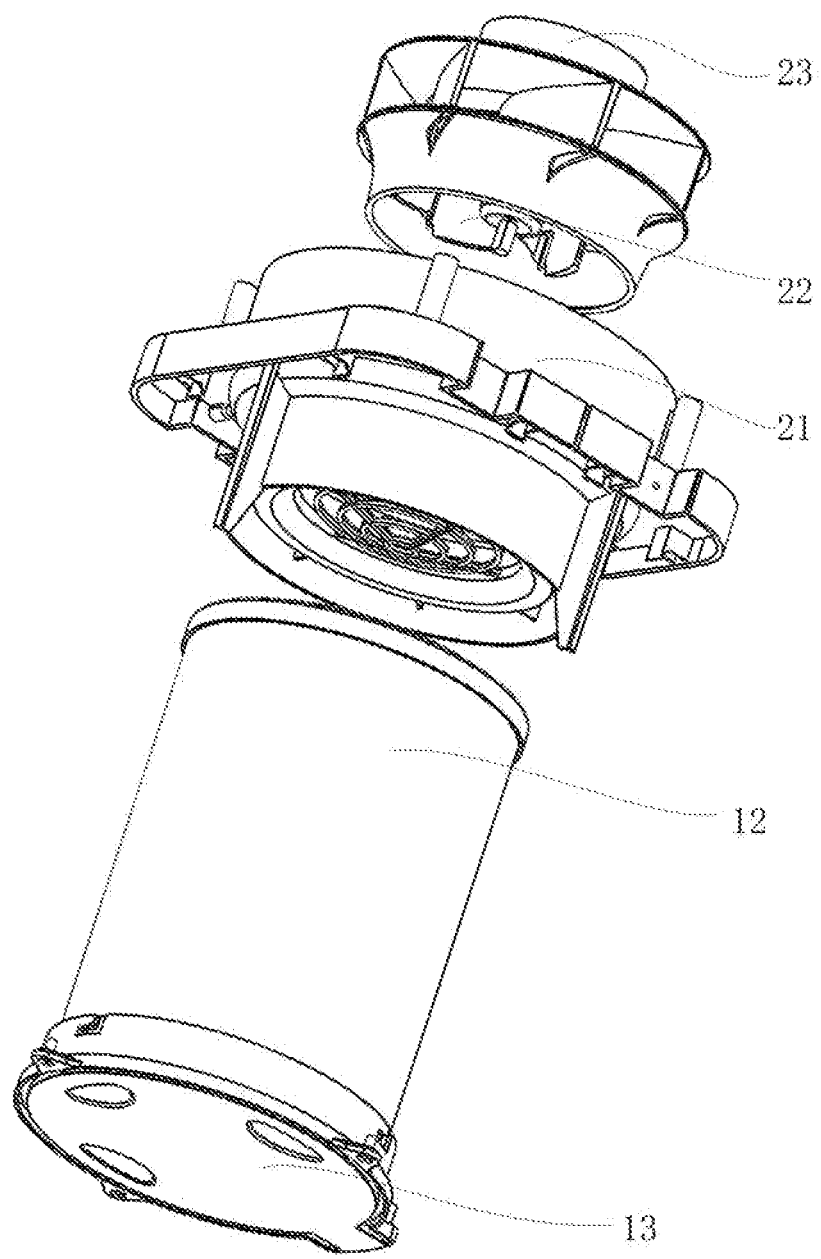
FIG. 17 illustrates an exploded view of a disinfection portion and an air suction device according to Embodiment 4 of the present disclosure.
Figure 18:
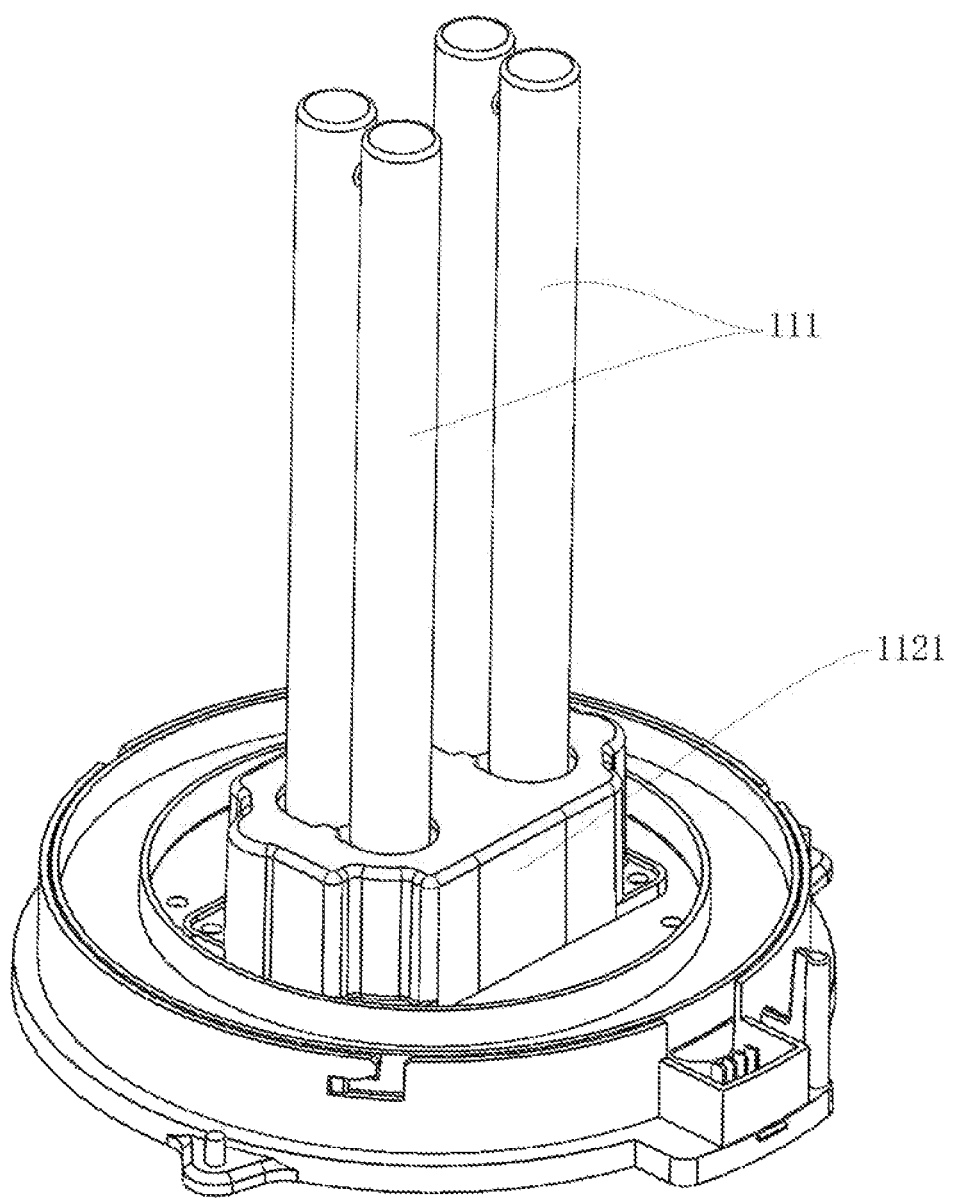
FIG. 18 illustrates a three-dimensional view of the purification device body and a mounting base according to Embodiment 4 of the present disclosure.
Figure 19:
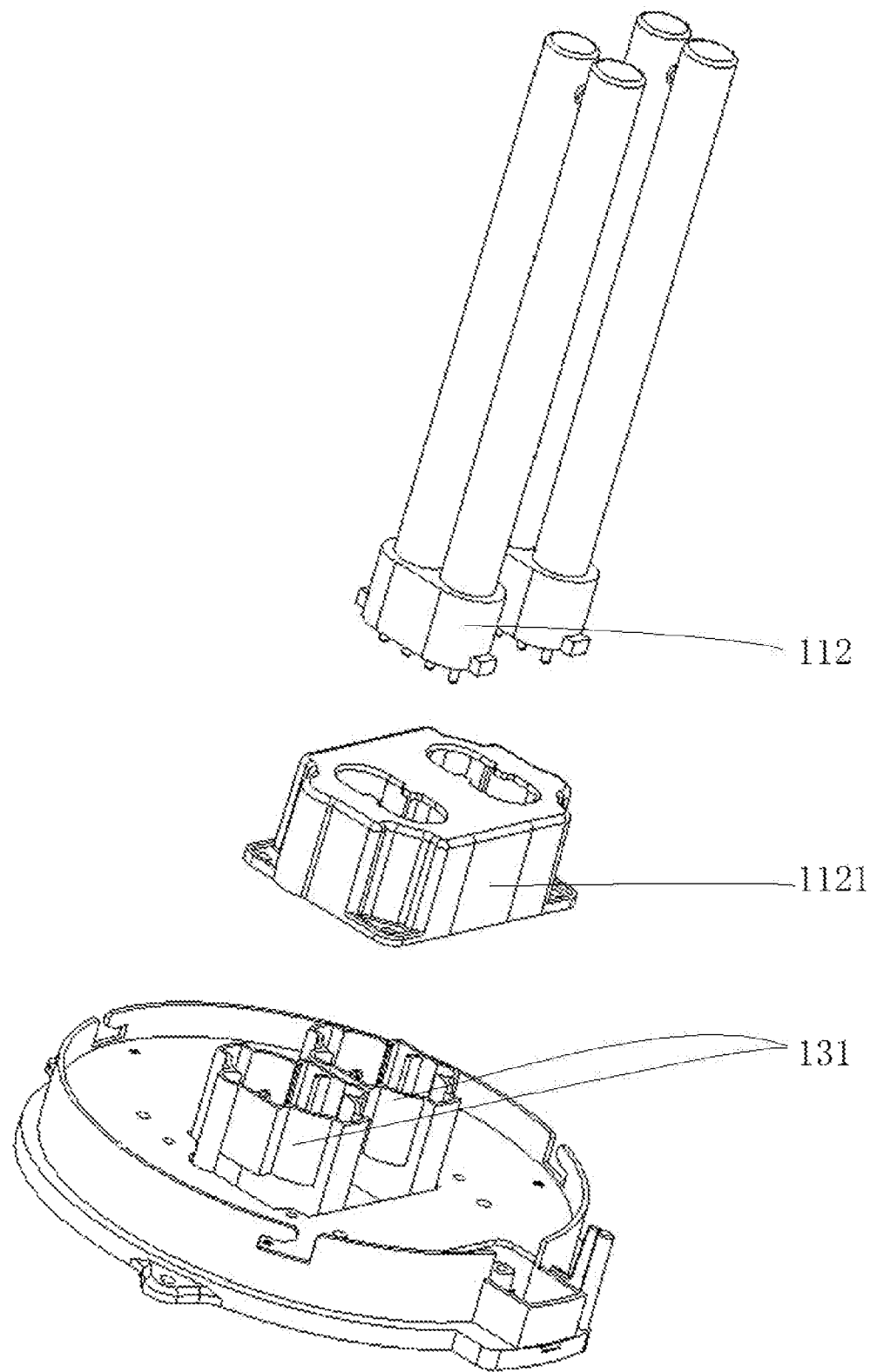
FIG. 19 illustrates an exploded view of the purification device body and the mounting base according to Embodiment 4 of the present disclosure.

As shown in FIG. 17, the purification device body 1 further includes a mounting base 13 correspondingly fitted. The mounting base 13 is provided with a lamp holder fixing portion 131 and a filter clamping portion 132. The lamp holder fixing portion 131 is located on an inner ring of the mounting base 13. The filter clamping portion 132 is located on an outer ring of the mounting base 13. The filter portion 12 is mounted through the filter clamping portion 132. A filter base 121 is disposed at a bottom of the filter portion 12. The filter base 121 is rotatably clamped and fixed with the filter clamping portion 132, so as to fix the filter portion 12 to the filter clamping portion 132.

Compared with Embodiment 1, the light shielding device 3 having the following structure is also omitted in this embodiment. In order to fix the top of the filter portion 12, the supporting frame 21 in the air suction device 2 directly is abutted against the filter portion 12 for fixing and mounting.

Embodiment 5

Figure 22:
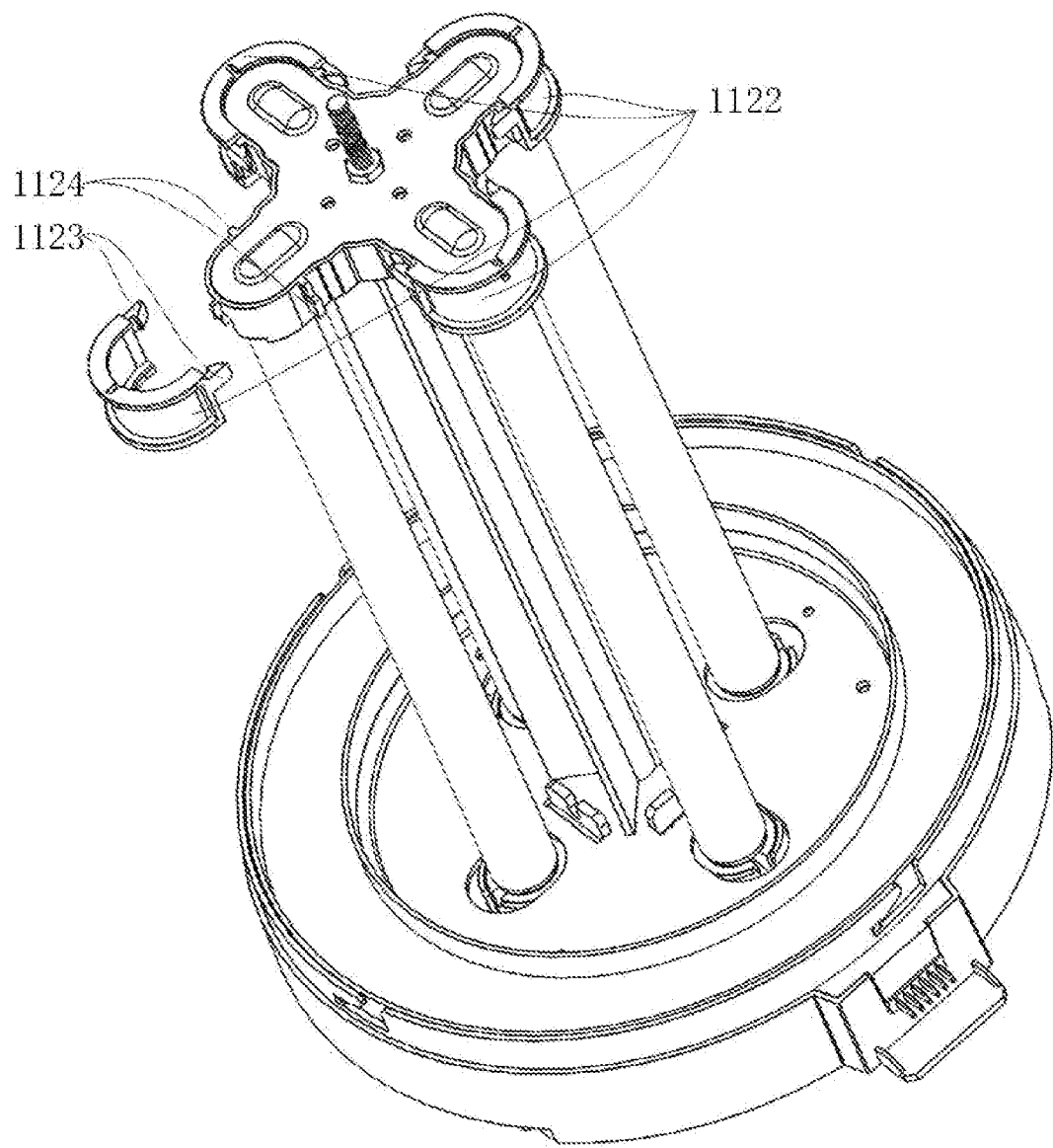
FIG. 22 illustrates an internal structure view of a purification device body according to Embodiment 5 of the present disclosure.

Compared with Embodiment 2, in this embodiment, as shown in FIG. 22, the four lamp holders 112 at the upper ends of the ultraviolet lamp tubes are all provided with corresponding lamp holder hoops 1122 for fixing the lamp tubes. Two ends of the lamp holder hoop 1122 are provided with protruding buckles 1123. Two sides of the lamp holder 112 are provided with clamping buckle plates 1124 corresponding to the buckles 1123. The clamping buckle plates 1124 are disposed symmetrically, and the clamping buckle plates 1124 are of L-shaped. The lamp holder hoop 1122 is fixed to the lamp holder 112 through the fit of the buckles 1123 and the clamping buckle plates 1124. The ultraviolet lamp tubes are fixed by means of the lamp holder hoops 1122, so as to prevent the ultraviolet lamp tubes from rotating and falling off.

The above are only the preferred embodiments of the present disclosure. It should be pointed out that those of ordinary skill in the art, without departing from the technical principle of the present disclosure, may also make several improvements and modifications. These improvements and modifications should also be regarded as the protection scope of the present disclosure.

What is claimed is:

1. A novel disinfection purifier, comprising: a purifier housing, and a purification device body and an air suction device disposed inside the purifier housing, wherein air passes through the purification device body by means of the air suction device and is sterilized;
    an air inlet is provided on a side wall of the purifier housing, or an air inlet is provided on a bottom of the purifier housing, or an air inlet is provided on a side wall of the purifier housing and a bottom of the purifier housing, and an air outlet is provided on a top of the purifier housing;
    the purification device body comprises a disinfection portion and a filter portion sleeving an outside of the disinfection portion, and external air enters the disinfection portion after being filtered by the filter portion under a suction of the air suction device and flows out from an upper part of the disinfection portion;
    the purification device body further comprises a mounting base and an upper fixing seat correspondingly fitted, the mounting base is provided with a lamp holder fixing portion and a filter clamping portion; the filter portion is mounted in fit with the upper fixing seat through the filter clamping portion;
    the novel disinfection purifier comprises a plurality of ultraviolet light sources disposed in the disinfection portion, and a lamp holder is disposed at an end of a ultraviolet light source of the plurality of ultraviolet light sources; a clamping protrusion is disposed on a side wall of the lamp holder at a lower end of the ultraviolet light source, and the lamp holder is clamped to a lamp holder clamping groove on the lamp holder fixing portion through the clamping protrusion;
    the air suction device is located on an upper part of the purification device body.

2. The novel disinfection purifier as claimed in claim 1, wherein the lamp holder fixing portion is located on an inner ring of the mounting base, the filter clamping portion is located on an outer ring of the mounting base.

3. The novel disinfection purifier as claimed in claim 2, wherein a fixing bracket is disposed between the mounting base and the upper fixing seat, a fixing rod is penetrated through a middle of the fixing bracket, two ends of the fixing rod are connected and fixed with the mounting base and the upper fixing seat respectively, and the fixing bracket is abutted against the lamp holder at an upper end of an ultraviolet light source.

4. The novel disinfection purifier as claimed in claim 2, wherein a filter base is disposed at a bottom of the filter portion, and the filter base is rotatably clamped and fixed with the filter clamping portion, so as to fix the filter portion to the filter clamping portion.

5. The novel disinfection purifier as claimed in claim 2, wherein the mounting base is a sealing structure, a power terminal is disposed at a side of the mounting base, and the power terminal supplies power to the ultraviolet light source.

6. The novel disinfection purifier as claimed in claim 3, wherein the fixing bracket comprises a plurality of supporting ribbed plates, the plurality of supporting ribbed plates are disposed on a side wall of the fixing bracket, an upper part of the supporting ribbed plate is abutted against the lamp holder at the upper end of the ultraviolet light source, a positioning protrusion is disposed on a lower part of the supporting ribbed plate, and the positioning protrusion is correspondingly fitted to a positioning hole provided on the mounting base.

7. The novel disinfection purifier as claimed in claim 3, wherein the ultraviolet light source comprises four ultraviolet light tubes, four lamp holders at upper ends of the four ultraviolet light tubes are integrally disposed in a cross shape, and an upper end of the fixing rod passes through a central position of the four lamp holders and is connected with the upper fixing seat.

8. The novel disinfection purifier as claimed in claim 1, wherein the lamp holder fixing portion is located on an inner ring of the mounting base, the filter clamping portion is located on an outer ring of the mounting base;
    a filter base is disposed at a bottom of the filter portion, and the filter base is rotatably clamped and fixed with the filter clamping portion, so as to fix the filter portion to the filter clamping portion.

9. The novel disinfection purifier as claimed in claim 8, wherein the mounting base is a sealing structure, a power terminal is disposed at a side of the mounting base, and the power terminal supplies power to the ultraviolet light source;
    the ultraviolet light source comprises at least two ultraviolet light tubes, the ultraviolet light tubes are inserted and fixed to the lamp holder fixing portion through a lamp holder located at one end of ultraviolet light source, and the lamp holder is covered and fixed by a lamp holder cover.

10. The novel disinfection purifier as claimed in claim 1, wherein the air suction device comprises a supporting frame, and a fan and a motor fixed within the supporting frame, and the novel disinfection purifier comprises a light shading device, the light shading device is disposed between the air suction device and the purification device body.

11. The novel disinfection purifier as claimed in claim 10, wherein the light shading device comprises a plurality of conical baffles sleeved at intervals from inside to outside.

12. The novel disinfection purifier as claimed in claim 1, wherein the purifier housing comprises four supporting columns located at top corners of the purifier housing, a plurality of housing plates, a housing base, and a housing top cover, the supporting columns fix the housing top cover, the air suction device, the purification device body, and the housing base successively from top to bottom, and the housing plates are fixed by the supporting columns and form an outer wall of the purifier housing.

13. The novel disinfection purifier as claimed in claim 12, further comprising: a control device and a detection device, wherein the control device is disposed on an upper part of the housing top cover, the detection device is disposed on the housing plate, the control device comprises a display panel and a control knob, the detection device comprises a detection mounting cover plate and an air quality sensor, and the housing top cover is further provided with a dustproof hood for protection.

14. The novel disinfection purifier as claimed in claim 1, wherein the filter portion comprises a barrel-shaped HEPA filter screen.

15. The novel disinfection purifier as claimed in claim 7, wherein each of the four lamp holders at the upper ends of the four ultraviolet lamp tubes is provided with a lamp holder hoop for fixing a corresponding lamp tube; and two ends of the lamp holder hoop are provided with protruding buckles, two sides of the lamp holder are provided with clamping buckle plates corresponding to the buckles, and the lamp holder hoop is fixed to the lamp holder through a fit of the buckles and the clamping buckle plates.

\* \* \* \* \*